United States Patent [19]

Tuttle

[11] Plant 4,060

[45] June 14, 1977

[54] APPLE TREE—MUTATION OF SCARLET STAYMARED

[75] Inventor: Roy Tuttle, Greenfield, Ind.

[73] Assignee: Stark Brothers Nurseries and Orchards Co., Louisiana, Mo.

[21] Appl. No.: 690,388

[22] Filed: May 27, 1976

[51] Int. Cl.[2] ..... A01H 5/03

[52] U.S. Cl. ..... Plt./34

*Primary Examiner*—Robert E. Bagwill

*Attorney, Agent, or Firm*—Burns, Doane, Swecker & Mathis

[57] ABSTRACT

The new and distinct variety of apple tree is a mutation of the Scarlet Staymared apple tree. The apple of the new variety has a deeper overall red color, no scarf skin, and a smoother skin and much less tendency to crack.

1 Drawing Figure

APPLE TREE—MUTATION OF SCARLET STAYMARED

SUMMARY OF THE INVENTION

This invention relates to improvements in Apple Trees of the Staymared type.

The new variety which is a mutation of the Scarlet Staymared apple tree was found by me during 1964 while searching for highly colored fruit for exhibition among trees of the Scarlet Staymared variety growing on a farm in Hancock County, Ind. I was attracted to the new variety because of the distinctive color of its fruit. Asexual reproduction of my discovery has been performed. This propagation shows that the unique combination of characteristics and distinctive color come true to form and are established and transmitted through succeeding propagations.

BRIEF DESCRIPTION OF THE DRAWINGS

The accompanying drawing shows typical specimens of the foliage and fruit of the new variety as depicted in color as nearly true as is reasonably possible to make the same in a color illustration of this character.

DETAILED DESCRIPTION OF THE DISCLOSURE

The following is a detailed description of my new variety with color terminology in accordance with Ridgway's Color Standards and Nomenclature except where general color terms of ordinary dictionary significance are obvious.

The specimens described were grown at Louisiana, Mo.

The first and last picking was from about Oct. 10, 1975 through about Oct. 18, 1975.

Tree: Medium large; vigorous; upright; tall; open; rapid growing; hardy; productive; regular bearing.

Trunk: Medium stock; smooth.

Branches: Medium thick; smooth; much branching; brown — 2 year wood Olive Brown Plate XL, Color No. 17‴, tone *m* of Ridgway Color Standards.

*Lenticels.*—Few; medium large.

Leaves: Length, 3¼″; Width, 2¼″; medium large; wide; medium short; oval; abruptly pointed; thick; dark green — Forest Green Plate XVII, Color No. 29′, tone *m* of Ridgway Color Standards; rugose.

*Margin.*—Coarsely serrate.

*Petiole.*—Length, ⅞″; medium short; thick.

Flowers: Date of first and full bloom, 4/6/76 – 4/14/76; medium late; large, pink — Laelia Pink Plate XXXVIII, Color No. 67″, tone *d* of Ridgway Color Standards with white areas.

Fruit: Maturity when described eating hard ripe; Oct. 10, 1975.

*Size.*—Uniform; axial diameter 3″; transverse 3½″; conic; truncate at base.

*Cavity.*—Symmetrical; flaring toward apex; even; pubescent toward apex; depth: ½″; breadth: 1¼″; markings, green — Rainette Green Plate XXXI, Color No. 27″, tone *i* of Ridgway Color Standards.

*Basin.*—Symmetrical; flaring base; narrow; furrowed; depth: ⅝″; breadth: 1½″; markings, green — Rainette Green Plate XXXI, Color No. 27‴, tone *i* of Ridgway Color Standards.

Stem: Medium slender; pubescent.

*Length.*—¾″.

*Breadth.*—11/16″.

*Markings.*—Red tinge.

Calyx: Closed; segments persistent; broadly lanceolate.

*Length.*—⅛″; approximate; converged from base toward center.

*Outer Surface.*—Pubescent.

*Inner surface.*—Pubescent.

Skin: Thick; tough; glassy, when rubbed; waxed. Dots conspicuous; few; small; even; ruptured; circular. Color of dots: Buff — Pale Ochraceous Plate XV, tone *f* of Ridgway Color Standards. Distribution of dots: Most numerous toward basin. Color of markings: Dragons-blood Red Plate XIII, Color No. 5′, tone *f* of Ridgway Color Standards; blotched with Acajou Red Plate XIII, Color No. 1′, tone *i* of Ridgway Color Standards.

*Bloom.*—Wanting.

*General color effect.*—Bright red.

Flesh: Juicy; satiny; white with yellowish-greenish tint.

*Texture.*—Firm, tender, fine, crisp.

*Flavor.*—Subacid; sprightly; rich; distinct.

*Quality.*—Best.

Core: Median.

*Bundle area* (*Longitudinal section*).—Medium large; cordate. Symmetrical at base; acute at base.

*Halves of area.*—Unequal.

*Bundles.*—Green; inconspicuous; two whorls.

*Alternate bundle.*—Distant from calyx; reaches tube above stamens.

*Core lines.*—Clasping; indistinct; carpellary indistinct; small.

*Calyx-tube.*—Funnel-form.

*Stem of funnel.*—3/16″.

*Depth of tube to shoulder.*—2/16″.

*Entire depth.*—5/16″.

*Styles present.*—Pubescent; throughout.

*Stamens.*—One distinct whorl; median.

*Auxillary cavity.*—Present.

*Seed cells.*—Axile: closed.

*Cell walls.*—Approximate thin-tough.

*Length.*—⅞″.

*Breadth.*—½″.

*Longitudinal section oval.*—Obtuse at apex.

*Surface.*—Tufted; narrow.

Seeds: Number perfect: 4 to 8. Largest number in one cell: 2; length ⅜″.

*Breadth.*—3/16″.

*Form.*—Acuminate.

*Color.*—Mars Brown Plate X, Color No. 13′, tone *m* of Ridgway Color Standards.

Use: Market; dessert; culinary.

Keeping Quality: Good. Number of days in ordinary storage: 100.

I claim:

1. A new and distinct variety of apple tree which is a mutation of the Scarlet Staymared variety substantially as shown and described, characterized by the presence of less prominent lenticels and apples of a deeper overall red color having a smoother skin and less tendency to crack.

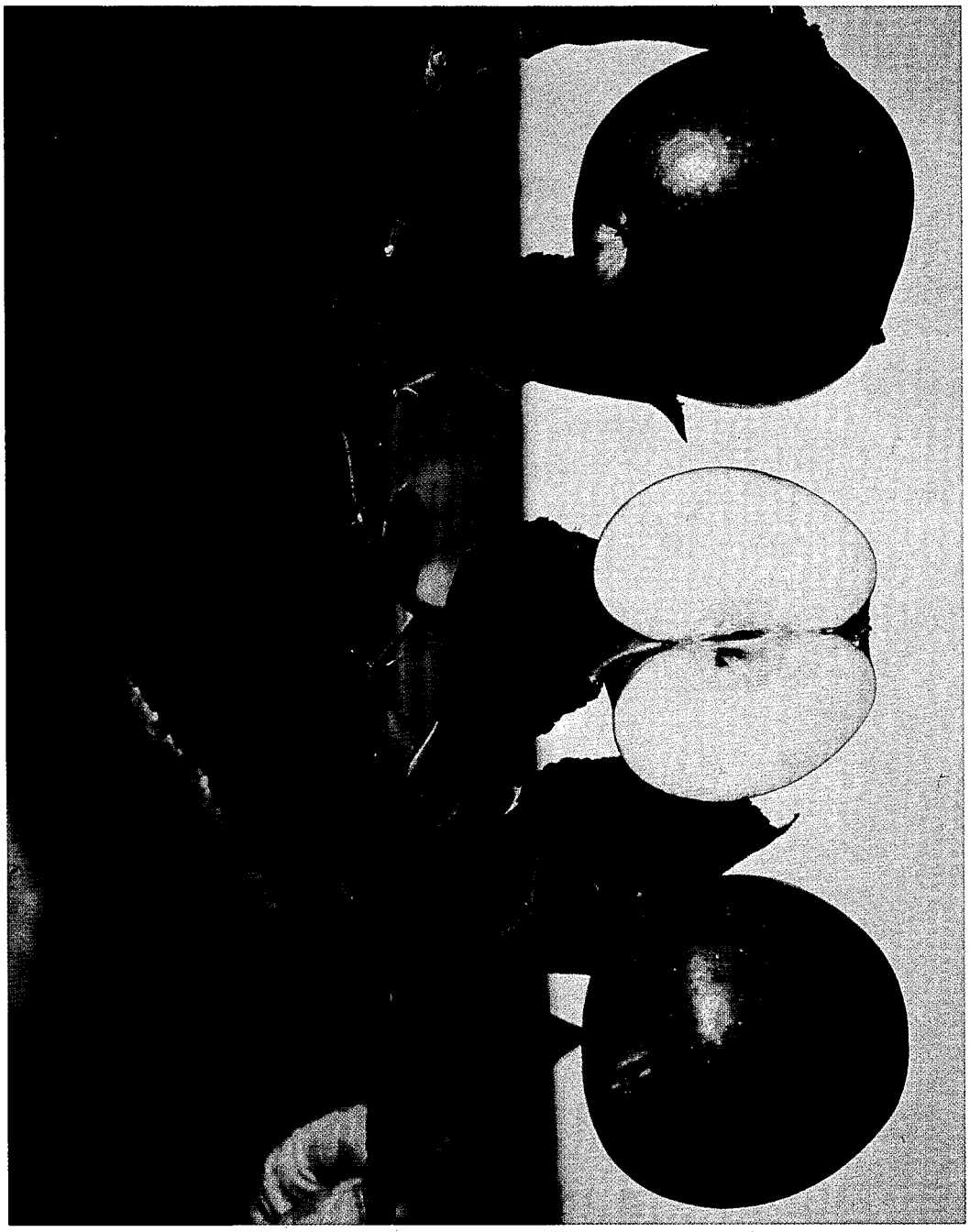

* * * * *